(12) United States Patent
Vaysse-Ludot et al.

(10) Patent No.: US 8,063,100 B2
(45) Date of Patent: Nov. 22, 2011

(54) PROCESS FOR THE SYNTHESIS OF STRONTIUM RANELATE AND ITS HYDRATES

(75) Inventors: Lucile Vaysse-Ludot, St-Wandrille-Rancon (FR); Jean-Pierre Lecouve, Le Havre (FR); Pascal Langlois, St-Jean-de-la-Neuville (FR)

(73) Assignee: Les Laboratoires Servier, Suresnes Cedex (FR)

( * ) Notice: Subject to any disclaimer, the term of this patent is extended or adjusted under 35 U.S.C. 154(b) by 626 days.

(21) Appl. No.: 12/284,695

(22) Filed: Sep. 24, 2008

(65) Prior Publication Data

US 2009/0082578 A1    Mar. 26, 2009

(30) Foreign Application Priority Data

Sep. 26, 2007   (FR) ...................................... 07 06731

(51) Int. Cl.
*A61K 31/381*  (2006.01)
*C07D 333/16*  (2006.01)

(52) U.S. Cl. ......................................... 514/447; 549/61

(58) Field of Classification Search .................. 514/447; 549/16
See application file for complete search history.

(56) References Cited

U.S. PATENT DOCUMENTS

2007/0292529 A1 * 12/2007 Tabbiner ...................... 424/601
2009/0082578 A1 * 3/2009 Vaysse-Ludot et al. ........ 549/61

* cited by examiner

*Primary Examiner* — Taofiq A Solola
(74) *Attorney, Agent, or Firm* — Hueschen and Sage

(57) ABSTRACT

A process for the industrial synthesis of strontium ranelate of formula (I):

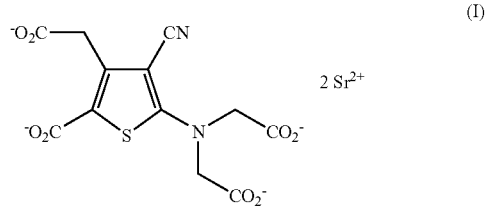

and its hydrates.

11 Claims, No Drawings

PROCESS FOR THE SYNTHESIS OF STRONTIUM RANELATE AND ITS HYDRATES

The present invention relates to a process for the synthesis of strontium ranelate of formula (I):

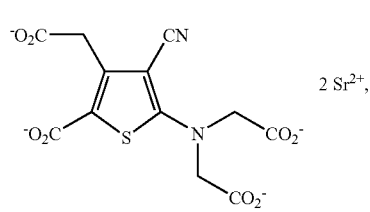

or the distrontium salt of 5-[bis(carboxymethyl)amino]-3-carboxymethyl-4-cyano-2-thiophenecarboxylic acid, and its hydrates.

Strontium ranelate has very valuable pharmacological and therapeutic properties, especially pronounced anti-osteoporotic properties, making this compound useful in the treatment of bone diseases.

Strontium ranelate, its preparation and its therapeutic use have been described in the European Patent Specification EP 0 415 850.

The patent specification EP 0 415 850 describes three methods for the synthesis of strontium ranelate.

The second of the methods described consists of heating at reflux the ethyl tetraester of formula (IIa):

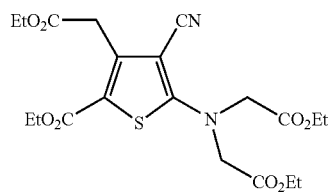

with sodium hydroxide, in an aqueous alcoholic medium, and then distilling off the ethanol and most of the water to isolate the tetrasodium salt of formula (IIIa) by precipitation:

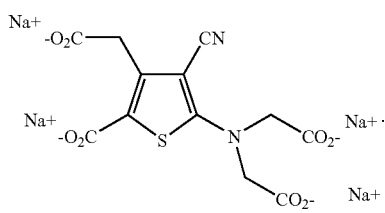

The compound of formula (IIIa) is then reacted with strontium chloride in water to yield strontium ranelate, which is isolated by filtration.

However, when operating under the conditions described for that second method, the Applicant has only obtained strontium ranelate in a yield of less than 70%.

The Applicant has developed an industrial synthesis process which makes it possible to obtain strontium ranelate in an excellent yield and with excellent purity.

More specifically, the present invention relates to a process for the synthesis of strontium ranelate of formula (I) starting from a compound of formula (II):

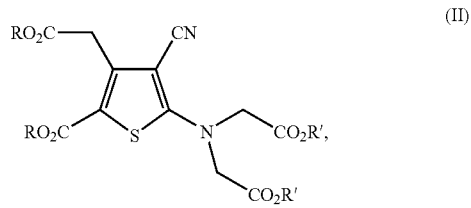

wherein R and R', which may be the same or different, each represent a linear or branched $(C_1-C_6)$alkyl group, preferably a methyl group,
which is reacted with sodium hydroxide or potassium hydroxide,
in water or in a mixture of water and an organic solvent,
at a temperature from 0 to 100° C.,
to yield the salt of formula (III):

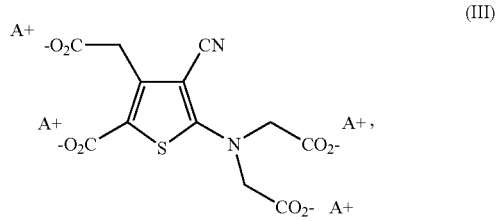

wherein A represents Na or K,
which is reacted with strontium chloride,
in a mixture of water and an organic solvent,
at a temperature from 0 to 100° C.,
to yield, after isolation, strontium ranelate or one of its hydrates.

Among the organic solvents there may be mentioned, by way of example, tetrahydrofuran, acetone, 2-methyl-tetrahydrofuran, dimethyl sulphoxide, acetonitrile, N-methylpyrrolidone and alcoholic solvents such as methanol, ethanol, isopropanol and isobutanol.

Surprisingly, the presence of an organic solvent in the step of salt conversion with strontium chloride makes it possible to increase the yield very substantially.

The amount of sodium hydroxide or potassium hydroxide is preferably greater than or equal to 4 moles per mole of compound of formula (II).

The temperature for the saponification reaction is preferably from 20 to 70° C.

In accordance with an embodiment of the present invention, the salt of formula (III) is isolated before reaction with strontium chloride.

In accordance with another embodiment, the solution of the salt of formula (III) is clarified before being used in the reaction with strontium chloride.

In accordance with another embodiment, the solution of the salt of formula (III) is used as such in the reaction with strontium chloride.

The amount of strontium chloride is preferably greater than or equal to 2 moles per mole of compound of formula (II).

The temperature of the reaction with strontium chloride is preferably from 20 to 50° C.

In the process according to the invention, the strontium ranelate is preferably isolated by filtration. The isolation of the strontium ranelate by filtration is preferably followed by one or more steps of washing with water, with an organic solvent or with a water/organic solvent mixture, and by a drying step.

The potassium salt of formula (IIIb), a particular case of the compounds of formula (III) wherein A represents K:

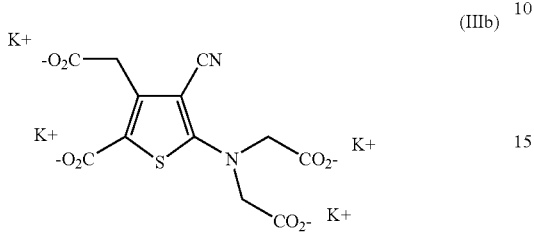

(IIIb)

is a new compound, useful as a synthesis intermediate in the chemical or pharmaceutical industry, especially in the synthesis of strontium ranelate and its hydrates, and by that token it forms an integral part of the present invention.

The Examples hereinbelow illustrate the invention.

EXAMPLE 1

Distrontium salt of 5-[bis(carboxymethyl)amino]-3-carboxymethyl-4-cyano-2-thiophenecarboxylic acid At 20-25° C., load an 800 ml reactor, provided with a temperature probe and an impeller, with 50 g of methyl 5-[bis(2-methoxy-2-oxoethyl)-amino]-4-cyano-3-(2-methoxy-2-oxoethyl)-2-thiophenecarboxylate and 75 ml of tetrahydrofuran.

Start stirring and then load the reactor with an aqueous solution of sodium hydroxide prepared beforehand using 22.9 g of NaOH and 216 ml of water.

Keep stirring the reaction mixture for from 4 to 6 hours.

Add an aqueous solution of strontium chloride prepared beforehand using 73.9 g of $SrCl_2$ and 340 ml of water.

Keep stirring for 20 hours at from 20 to 25° C.

The suspension slowly becomes more pronounced (fine yellow suspension).

Filter over a no. 3 frit of 100 mm diameter (very rapid filtration), and immediately wash through the frit with 2×50 ml of water.

Remove volatile components from the product for 30 minutes in vacuo. Dry in a ventilated oven at 30° C.

The strontium ranelate is thereby obtained in a yield of 93.8%.

EXAMPLE 2

Distrontium salt of 5-[bis(carboxymethyl)amino]-3-carboxymethyl-4-cyano-2-thiophenecarboxylic acid.

The process used is that described in Example 1, the tetrahydrofuran being replaced by acetone.

The strontium ranelate is thereby obtained in a yield of 92.6%.

EXAMPLE 3

Distrontium salt of 5-[bis(carboxymethyl)amino]-3-carboxymethyl-4-cyano-2-thiophenecarboxylic acid The process used is that described in Example 1, the sodium hydroxide being replaced by 32.1 g of KOH.

The solution of the potassium salt of formula (IIIb) is clarified before the reaction with strontium chloride.

The strontium ranelate is thereby obtained in a yield of 94%.

EXAMPLE 4

Distrontium salt of 5-[bis(carboxymethyl)amino]-3-carboxymethyl-4-cyano-2-thiophenecarboxylic acid The process used is that described in Example 1, the tetrahydrofuran being replaced by isopropanol.

The strontium ranelate is thereby obtained in a yield of 94.8%.

EXAMPLE 5

Distrontium salt of 5-[bis(carboxymethyl)amino]-3-carboxymethyl-4-cyano-2-thiophenecarboxylic acid At 20-25° C., load an 800 ml reactor, provided with a temperature probe and an impeller, with 22.9 g of NaOH and 500 ml of water. Start stirring and load the reactor with 50 g of methyl 5-[bis(2-methoxy-2-oxoethyl)-amino]-4-cyano-3-(2-methoxy-2-oxoethyl)-2-thiophenecarboxylate.

Heat the mixture to 70° C. over 30 minutes and maintain at that temperature for 25 minutes, and then clarify at 70° C. over a frit of porosity 4 and of 75 mm diameter and rinse with 50 ml of water.

Re-load the above clear orange filtrate into an 800 ml reactor.

Cool the reaction mixture to 20° C., and add 75 ml of ethanol and then, over 15 minutes, a solution, prepared beforehand, of 73.9 g of $SrCl_2$ in 137 ml of water.

Stir for 2 hours at from 20 to 25° C.

The suspension slowly becomes more pronounced (fine yellow suspension).

Filter over a no. 3 frit of 100 mm diameter (instantaneous filtration) and immediately re-filter over the frit with 2×250 ml of water. Dry in a ventilated oven at 30° C.

The strontium ranelate is thereby obtained in a yield of 94%.

EXAMPLE 6

Distrontium salt of 5-[bis(carboxymethyl)amino]-3-carboxymethyl-4-cyano-2-thiophenecarboxylic acid Step A: Potassium salt of 5-[bis(carboxymethyl)amino]-3-carboxymethyl-4-cyano-2-thiophenecarboxylic acid Compound of Formula (IIIb)

At 20-25° C., load an 800 ml reactor, provided with a temperature probe and an impeller, with 40.4 g of KOH and 225 ml of water.

Start stirring and then load the reactor with 60 g of methyl 5-[bis(2-methoxy-2-oxoethyl)-amino]-4-cyano-3-(2-methoxy-2-oxoethyl)-2-thiophenecarboxylate and 50 ml of water.

Heat the reaction mixture to 55-60° C. over 30 minutes and keep stirring it for 2 hours.

Carry out clarification at 60° C. and then cool the reaction mixture to 20-25° C. Dry at 40° C. in vacuo. To the residue thereby obtained add 200 ml of ethyl acetate and 20 ml of methanol. Stir for 8 hours. Filter the suspension obtained.

Remove volatile components from the product for 30 minutes in vacuo. Dry in a ventilated oven at 30° C.

Step B: Distrontium salt of 5-[bis(carboxymethyl)amino]-3-carboxymethyl-4-cyano-2-thiophenecarboxylic acid To 62.0 g of the potassium salt obtained in the preceding Step add 75 ml of tetrahydrofuran and 216 ml of water, and then an aqueous strontium chloride solution prepared beforehand using 73.9 g of $SrCl_2$ and 340 ml of water.

Stir for 20 hours at from 20 to 25° C.

The suspension slowly becomes more pronounced. Filter over a no. 3 frit of 100 mm diameter and wash through the frit immediately using 2×50 ml of water.

Remove volatile components from the product for 30 minutes in vacuo. Dry in a ventilated oven at 30° C.

The invention claimed is:

1. A process for the synthesis of strontium ranelate of formula (I):

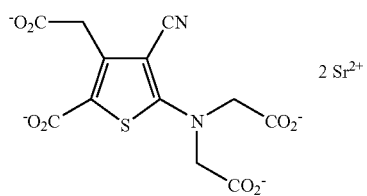

(I)

or a hydrate thereof,
wherein a compound of formula (II):

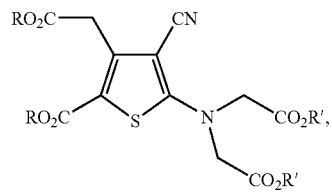

(II)

wherein R and R', which may be the same or different, each represent a linear or branched $(C_1-C_6)$alkyl group,
is reacted with sodium hydroxide or potassium hydroxide,
in water or in a mixture of water and an organic solvent,
at a temperature from 0 to 100° C.,
to yield a salt of formula (III):

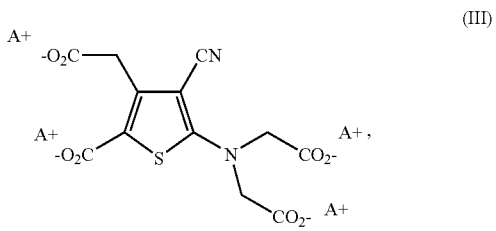

(III)

wherein A represents Na or K,
which is reacted with strontium chloride,
in a mixture of water and an organic solvent,
at a temperature from 0 to 100° C.,
to yield, after isolation, strontium ranelate of formula (I) or a hydrate thereof.

2. The process of claim 1, wherein the amount of sodium hydroxide or potassium hydroxide is greater than or equal to 4 moles per mole of the compound of formula (II).

3. The process of claim 1, wherein the temperature of the saponification reaction of the compound of formula (II) is from 20 to 70° C.

4. The process of claim 1, wherein the salt of formula (III) is isolated before reaction with strontium chloride.

5. The process of claim 1, wherein the solution of the salt of formula (III) is clarified before being used in the reaction with strontium chloride.

6. The process of claim 1, wherein the solution of the salt of formula (III) is used as such in the reaction with strontium chloride.

7. The process of claim 1, wherein the amount of strontium chloride is greater than or equal to 2 moles per mole of the compound of formula (II).

8. The process of claim 1, wherein the temperature of the salt conversion reaction of the compound of formula (II) is from 20 to 50° C.

9. The process of claim 1, wherein the strontium ranelate is isolated by filtration.

10. The process of claim 9, wherein the filtration step is followed by one or more washing steps and a drying step.

11. The process of claim 1, wherein R and R' each represent a methyl group.

* * * * *

UNITED STATES PATENT AND TRADEMARK OFFICE
CERTIFICATE OF CORRECTION

PATENT NO. : 8,063,100 B2  Page 1 of 1
APPLICATION NO. : 12/284695
DATED : November 22, 2011
INVENTOR(S) : Lucile Vaysse-Ludot It is certified that error appears in the above-identified patent and that said Letters Patent is hereby corrected as shown below:

IN THE CLAIMS:

Column 6, Line 39, In Claim 8: "formula (II)" should be -- formula (III) --.

Signed and Sealed this
Tenth Day of January, 2012

David J. Kappos
*Director of the United States Patent and Trademark Office*